US007289852B2

(12) United States Patent
Helfinstine et al.

(10) Patent No.: US 7,289,852 B2
(45) Date of Patent: Oct. 30, 2007

(54) IMPLANTABLE MEDICAL DEVICE CONFIGURED FOR DIAGNOSTIC EMULATION THROUGH SERIAL COMMUNICATION

(75) Inventors: Alan R. Helfinstine, Brooklyn Center, MN (US); Steve Jensen, Andover, MN (US)

(73) Assignee: Medtronic. Inc., Minneapolis, MN (US)

( * ) Notice: Subject to any disclaimer, the term of this patent is extended or adjusted under 35 U.S.C. 154(b) by 496 days.

(21) Appl. No.: 10/955,596

(22) Filed: Sep. 30, 2004

(65) Prior Publication Data

US 2005/0066088 A1 Mar. 24, 2005

Related U.S. Application Data

(63) Continuation of application No. 10/872,709, filed on Jun. 21, 2004, which is a continuation of application No. 09/596,173, filed on Jun. 16, 2000, now Pat. No. 6,754,533.

(51) Int. Cl.
*A61N 1/37* (2006.01)
(52) U.S. Cl. .............................. 607/27; 607/32; 607/30
(58) Field of Classification Search .................... 607/9, 607/16, 27, 30, 32, 57, 60, 31, 59
See application file for complete search history.

(56) References Cited

U.S. PATENT DOCUMENTS 4,532,930 A   8/1985   Crosby et al.

6,754,533 B1 * 6/2004 Helfinstine et al. ........... 607/27

OTHER PUBLICATIONS

U.S. Appl. No. 10/872,709, filed Jun. 21, 2004, Alan Helfinstine et al.

* cited by examiner

Primary Examiner—George R. Evanisko
(74) Attorney, Agent, or Firm—Fredrikson & Byron, P.A.

(57) ABSTRACT

An implantable medical device (IMD) with internal processor is configured for diagnostic emulation using an external processor coupled to the internal processor through a high speed serial link. The native external processor parallel data and address bus content can be converted to a serial communications stream, sent into the device, converted back to parallel address and data bus formats, and used to drive the device in place of the internal processor. The serial communication allows use of a small number of contact pads, conductors, or feed-throughs, depending on the device. Some devices allow serialized communication through the feed-through typically used for electrical stimulation. The devices can be used to enhance diagnostic testing with capabilities such as faster testing and more realistic testing. The IMD can be a wide variety of implantable devices such as neuro stimulators, pace makers, defibrillators, drug delivery pumps, diagnostic recorders, cochlear implants, and the like. The device can have a bus switch, which when activated, decouples the internal processor, and couples address and data buses containing information and commands provided by the external emulator through the serial communication channel.

27 Claims, 13 Drawing Sheets

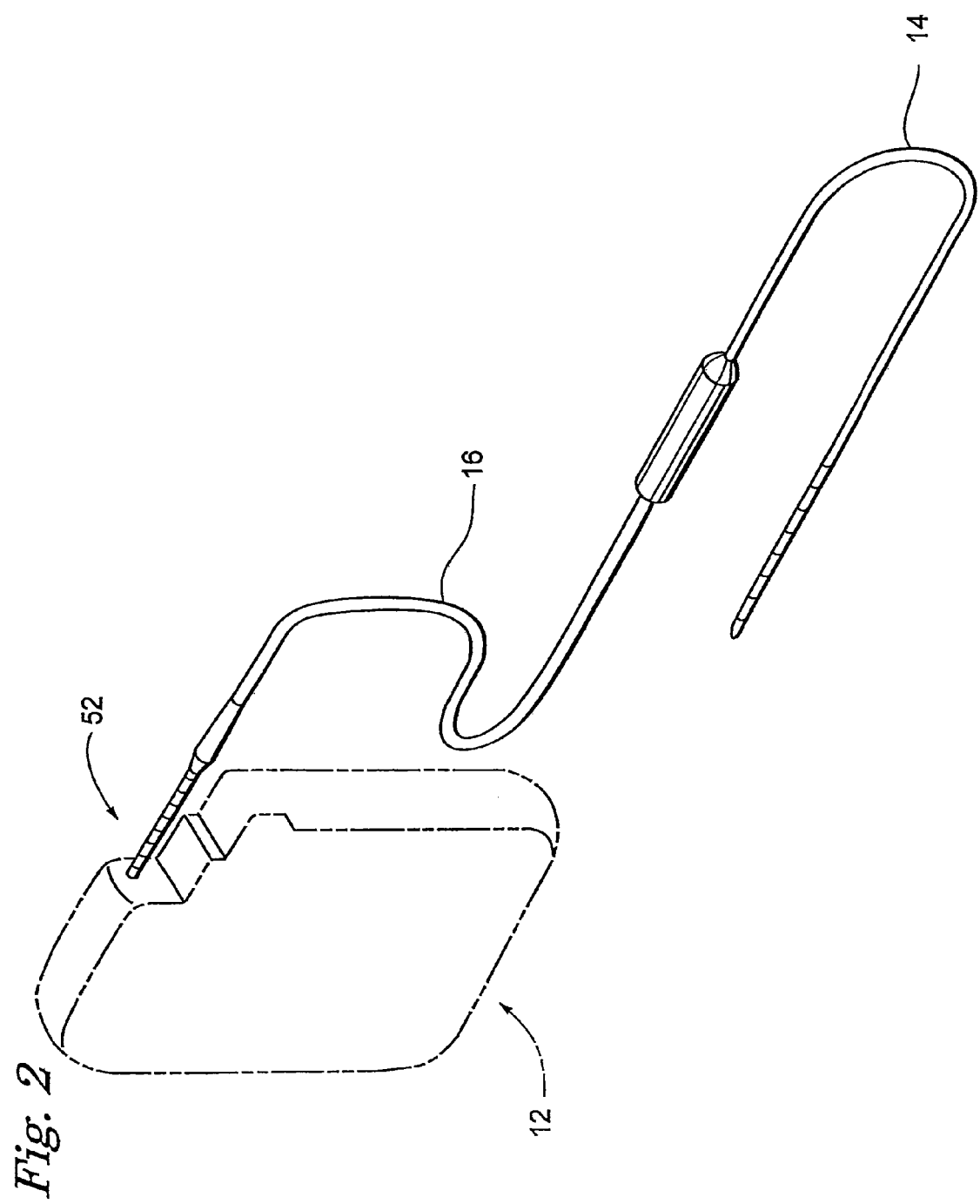

IMPLANTABLE MEDICAL DEVICE CONFIGURED FOR DIAGNOSTIC EMULATION THROUGH SERIAL COMMUNICATION

RELATED APPLICATIONS

The present application is a continuation-in-part of U.S. application Ser. No. 10/872,709, filed Jun. 21, 2004, titled IMPLANTABLE MEDICAL DEVICE CONFIGURED FOR DIAGNOSTIC EMULATION, which is a continuation of U.S. application Ser. No. 09/596,173, filed Jun. 16, 2000, titled IMPLANTABLE MEDICAL DEVICE CONFIGURED FOR DIAGNOSTIC EMULATION, now U.S. Pat. No. 6,754,533, all herein incorporated by reference.

BACKGROUND

This disclosure relates to a medical device and more specifically to an implantable medical device having an internal processor that executes software.

The medical device industry produces a wide variety of electronic and mechanical devices for treating patient medical conditions. Depending upon medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only, therapy to restore an individual to a more healthful condition and a fuller life. Many implantable medical devices have an internal processor that executes software.

Implantable medical devices with an internal processor typically include neuro stimulators, pacemakers, defibrillators, drug delivery pumps, and diagnostic recorders. The processor executes software to perform functions that can include telemetry, power management, physiological sensing, data recording, therapy delivery, and therapy measurement. As implantable medical devices have increased in sophistication, the software executed by the internal processor has also increased in complexity, and the task of debugging the software has increased in complexity The internal processor meets these demands while operating under a variety of constraints such as power, size, memory, speed, and the like that limit the processor's ability to perform functions other than those required for normal medical device operation. When the internal processor is tasked to perform functions not required for normal medical device operation such as developmental testing, production conformance testing, diagnostics testing, the internal processor can require a significant amount of time to perform these functions. Previous efforts to perform testing included constructing a laboratory model of the implantable medical device using different components to reduce constraints such as power, size, memory, and speed. Although a laboratory module can simulate testing, there are still differences between performance of the laboratory model and performance of the implantable medical device. The time requirements for the internal processor to perform testing can delay production and require compromises to desirable testing protocols. The results for these constraints can be increased costs, increased production time, discrepancies between laboratory product tests and production product tests, and decreased discretionary testing.

For the foregoing reasons there is a need for an implantable medical device to be configured to perform medical device functions with an internal processor and perform testing and diagnostics in another fashion.

An implantable medical device having a processor may have address and data busses of 8 or 16 bits each. If these busses are to be accessed from an external device, then a corresponding number of contact points and even feedthroughs may be required for the external emulation. What would be desirable is an implantable medical device allowing external emulator control of 8 bit wide (or wider) busses while requiring a much smaller number of contact points and feedthroughs. An implantable medical device supporting external emulation not requiring any additional feedthroughs would also be advantageous.

SUMMARY

An implantable medical device with internal processor is configured for diagnostic emulation with an external processor to enhance diagnostic testing by capabilities such as faster testing and more realistic testing. The external processor is coupleable to the medical device to execute software involving medical device components with a bus switch coupled to the address bus, the data bus, and the internal processor. The bus switch has a bus switch external connector that when activated is configured to couple an external processor through the address bus external connection to the address bus and couple the external processor through the data bus external connector to the data bus. When the external processor is coupled to the medical device, the internal processor is decoupled from the address bus and data bus.

The present invention can also include a medical device comprising an internal processor, an internal clock coupled to the internal processor, memory, a bus switch coupled to read and write the memory, a first address bus and first data bus coupled to the internal processor and the bus switch, as well as a second address bus and second data bus coupled to the bus switch. The bus switch can be adapted to receive an activation signal, whereas upon receiving the activation signal, the bus switch is configured to couple the second address bus and second data bus to the memory, and effectively decouple the first address bus and first data bus from the memory. The medical device can also include a serial-parallel interface having a serial communications port and a parallel port, where the parallel port can be coupled to the second address bus and the second data bus. The serial-parallel interface can be configured to received a serial format address through the serial communications port and output a parallel format address to the second address bus through the parallel port. Some medical devices also include at least one interrupt line coupled to the serial-parallel interface, where the interface is configured to output data from the interrupt line, through the serial communications port, in serial format.

Some medical devices also include several electrically conductive lines coupled to the serial-parallel interface serial communication port and to a feed-through connector. A feed-through connector may be simply coupled to a medical device circuit board, located within a hermetically sealable housing, or located and extending through a hermetically sealed housing. A switch can be coupled to the stimulator output lines and through the serial-parallel interface serial communications port and to the feed-through connector. The switch can be configured to establish electrical continuity between a feed-through connector and either the serial-parallel interface serial communication port or the stimulator output lines, but not both at the same time. In this way, the serial-parallel interface serial communication port can be communicated with the feed through connector. This can allow the feed-through connector, connected to a medical lead, to be used instead to connect an external emulator to the medical device to control the medical device from the emulator.

The present invention can also provide a method for externally controlling an implantable medical device, the method including sending an activation signal to the IMD, thereby causing the IMD to decouple an internal processor and be in a mode for allowing an external device to read and write data to memory in the IMD at a speed substantially as fast as the internal processor. The method can include sending a first serial communications stream to the IMD including the address to be read, reading data from the address in the IMD, sending the data out in a second serial communications stream, and receiving the second serial communications stream externally to the IMD. The method may further include sending a third serial communication stream to the MD including an address and data to be written into the IMD at the address, and receiving a fourth serial communications stream from the IMD including data read from the address in the third serial communications stream.

The high speed serial communication link may thus be used to convert parallel format data and address bus content from an external emulator to a high speed serial stream, sent to the IMD in serial format, thus requiring a small number of pads pins or electrical conductors. The high speed serial communication stream can then be converted back into a parallel format and used to drive the IMD data and address buses in place of the internal processor. The high speed serial communication link can be fast enough to allow the external emulator to drive the address and data buses at substantially the same speed as the internal processor would drive these buses. The external emulator may be capable of executing instructions much faster than the internal processor, and use this extra capacity to multi-task and execute other tasks interleaved with the task of emulating the internal processor.

BRIEF DESCRIPTION OF THE DRAWINGS

FIG. 2 shows a medical device embodiment;

DETAILED DESCRIPTION

Figure 1A:
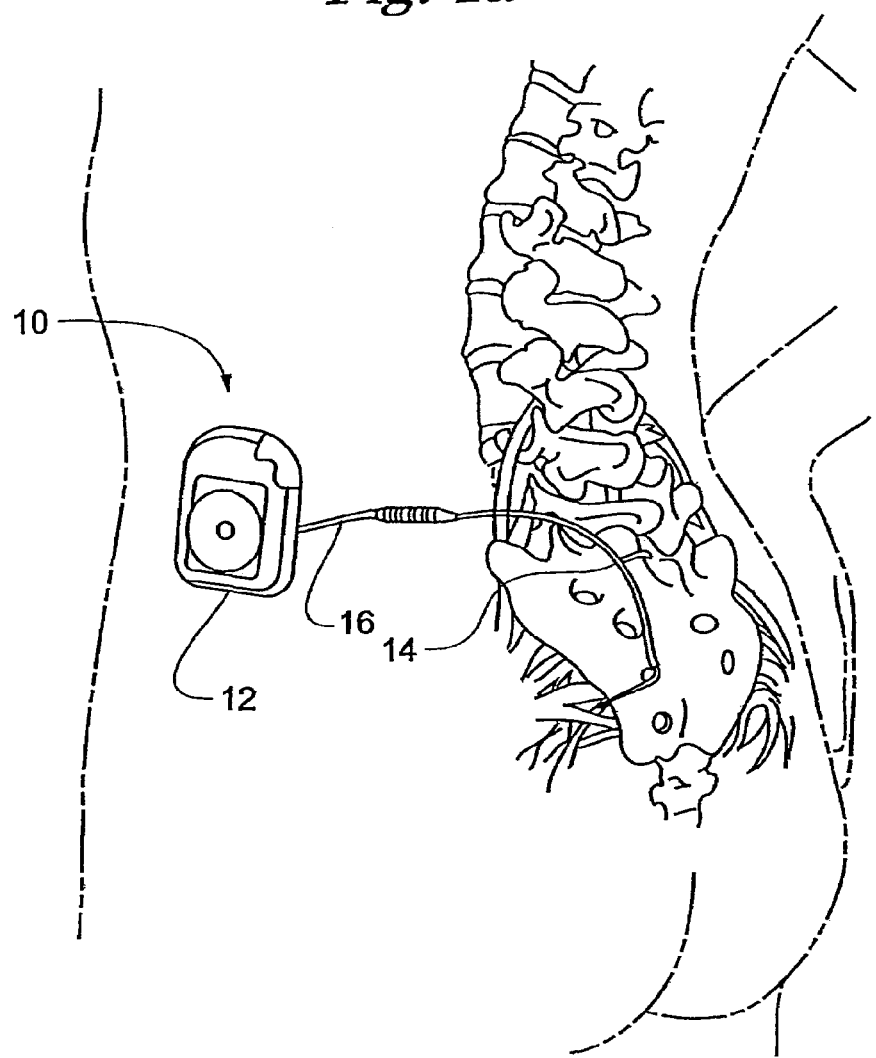
FIGS. 1A-1D show an environment of an implantable medical device.
Figure 1B:
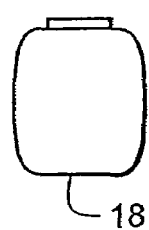
Figure 1C:
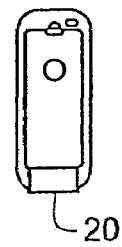
Figure 1D:
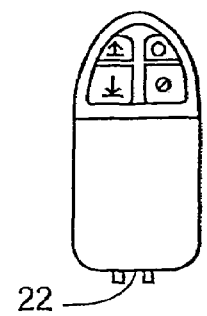

FIGS. 1a-1d show the general environment of an implantable medical device 10 and more specifically an Implantable Neuro Stimulator (INS) 12 embodiment that includes a lead 14, a lead extension 16, an External Neuro Stimulator (ENS) 18, a physician programmer 20, and a patient programmer 22. Although an INS 12 embodiment is shown, the implantable medical device 10 could also be a pacemaker, a defibrillator, a drug delivery pump, a diagnostic recorder, a cochlear implant, and the like.

Figure 3:
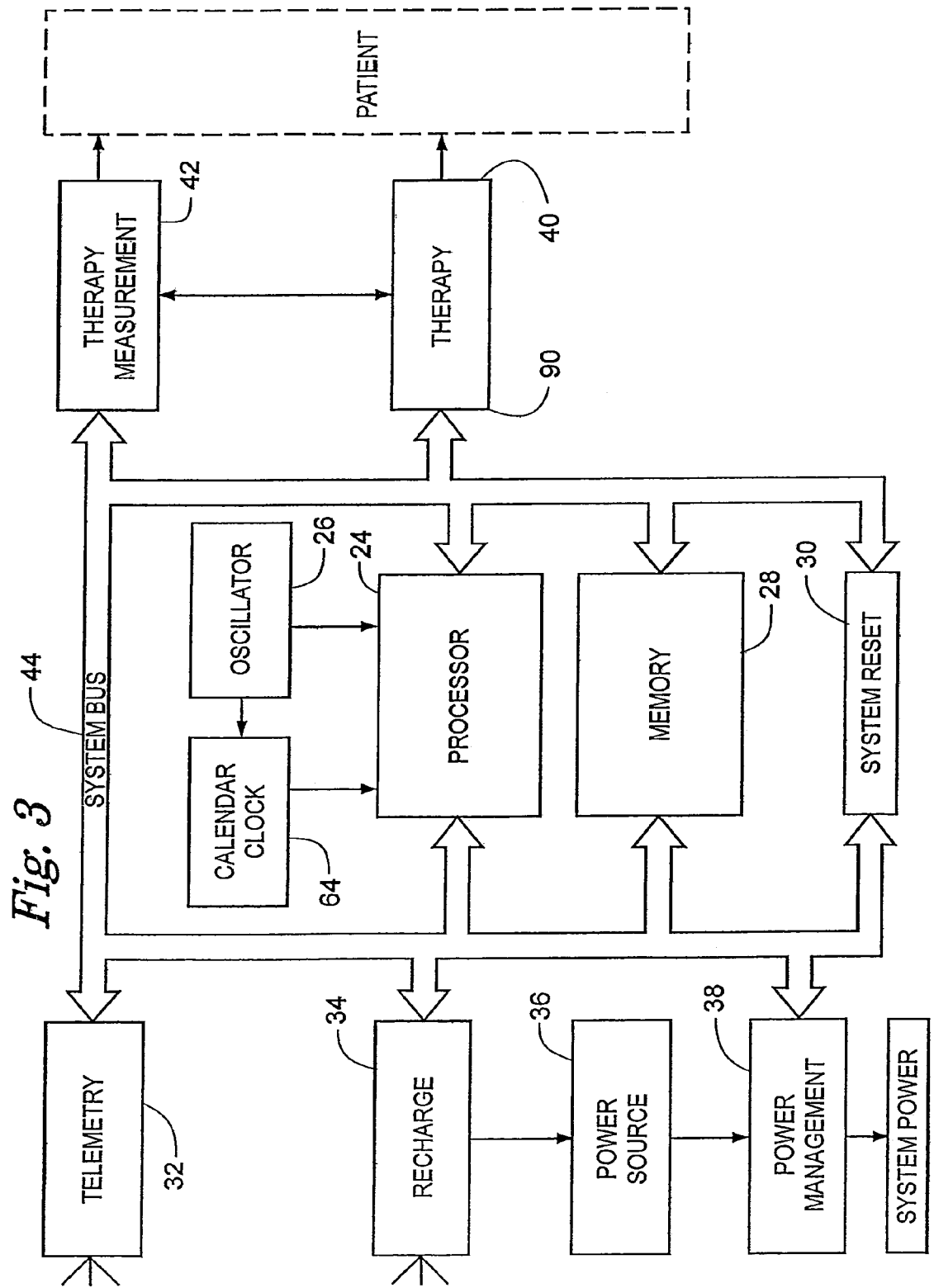
FIG. 3 shows a medical device block diagram embodiment.

FIG. 2 shows an Implantable Neuro Stimulator (INS) 12 medical device embodiment. FIG. 3 shows a block diagram of the INS 12 embodiment. The INS 12 generates a programmable electrical stimulation signal to influence a patient. The INS 12 comprises a processor 24 with an oscillator 26, memory 28, and system reset 30, a telemetry module 32, a recharge module 34, a power source 36, a power management module 38, a therapy module 40, and a therapy measurement module 42. Other versions of the INS 12 can include additional modules such as a diagnostics module. All components can be configured on one or more Application Specific Integrated Circuits (ASICs) except the power source 36. Also, all components are connected to bi-directional data bus 44 that is non-multiplexed with separate address 46 and data lines 48 (FIG. 6) except the oscillator 26, the calendar clock 64, and the power source 36. The system reset 30 controls operation of ASICs and modules during power up of the INS 12, so ASICs and modules registers can be loaded and brought on-line in a stable condition. The INS 12 can be configured in a variety of versions by removing modules not necessary for the particular configuration and by adding additional components or modules. Primary cell, non-rechargeable, versions of the INS 12 will not include some or all of the components in the recharge module 34. All component of the INS 12 are contained within or carried on a housing 50 that is hermetically sealed and manufactured from a biocompatible material such as titanium. Feedthroughs 52 provide electrical connectivity through the housing 50 while maintaining a hermetic seal, and the feedthroughs 52 can be filtered to reduce incoming noise from sources such as cell phones. The INS 12 operates according to hardware and software parameters.

Figure 4:
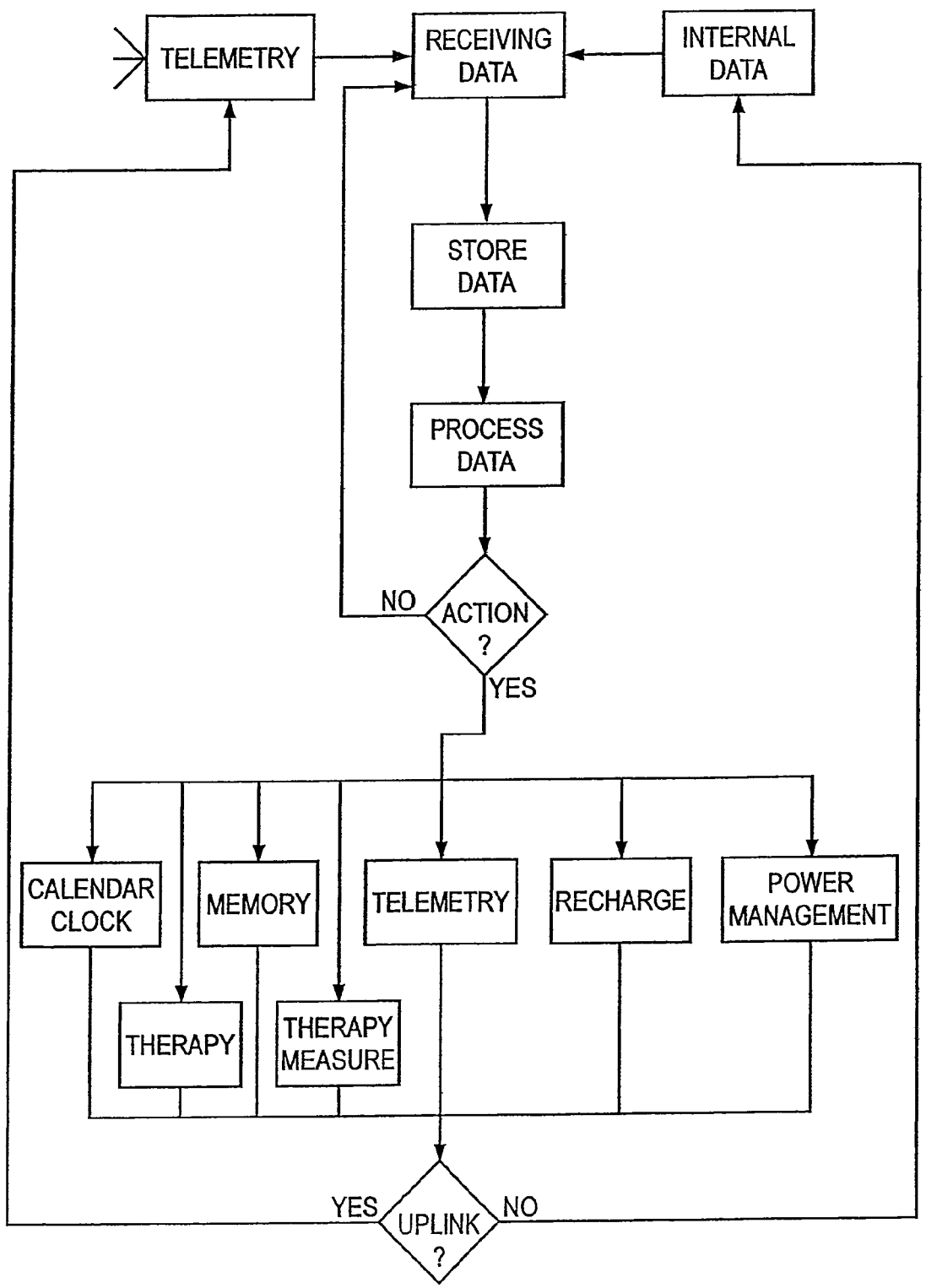
FIG. 4 shows a medical device basic operation flowchart embodiment.

FIG. 4 shows a basic INS 12 operation flowchart. Operation begins with when the processor 24 receives data from either telemetry or from an internal source in the INS 12. The received data is then stored in a memory 28 location. The data is processed by the processor 24 to identify the type of data and can include further processing such as validating the integrity of the data. After the data is processed, a decision is made whether to take an action. If no action is required, the INS stands by to receive data. If an action is required, the action will involve one or more of the following modules or components: calendar clock 64, memory 28, telemetry 32, recharge 34, power management 38, therapy 40, and therapy measurement 42. An example of an action would be to modify a programmed therapy. After the action is taken, a decision is made whether to prepare the action to be communicated, known as uplinked, to a patient programmer 22 or physician programmer 20 through the telemetry module 32. If the action is uplinked, the action is recorded in the patient programmer 22 or physician programmer 20.

If the action is not uplinked, the action is recorded internally within the INS 12. An INS 12 as well as other implantable medical devices 10 can be configured for diagnostic emulation.

Figure 5:
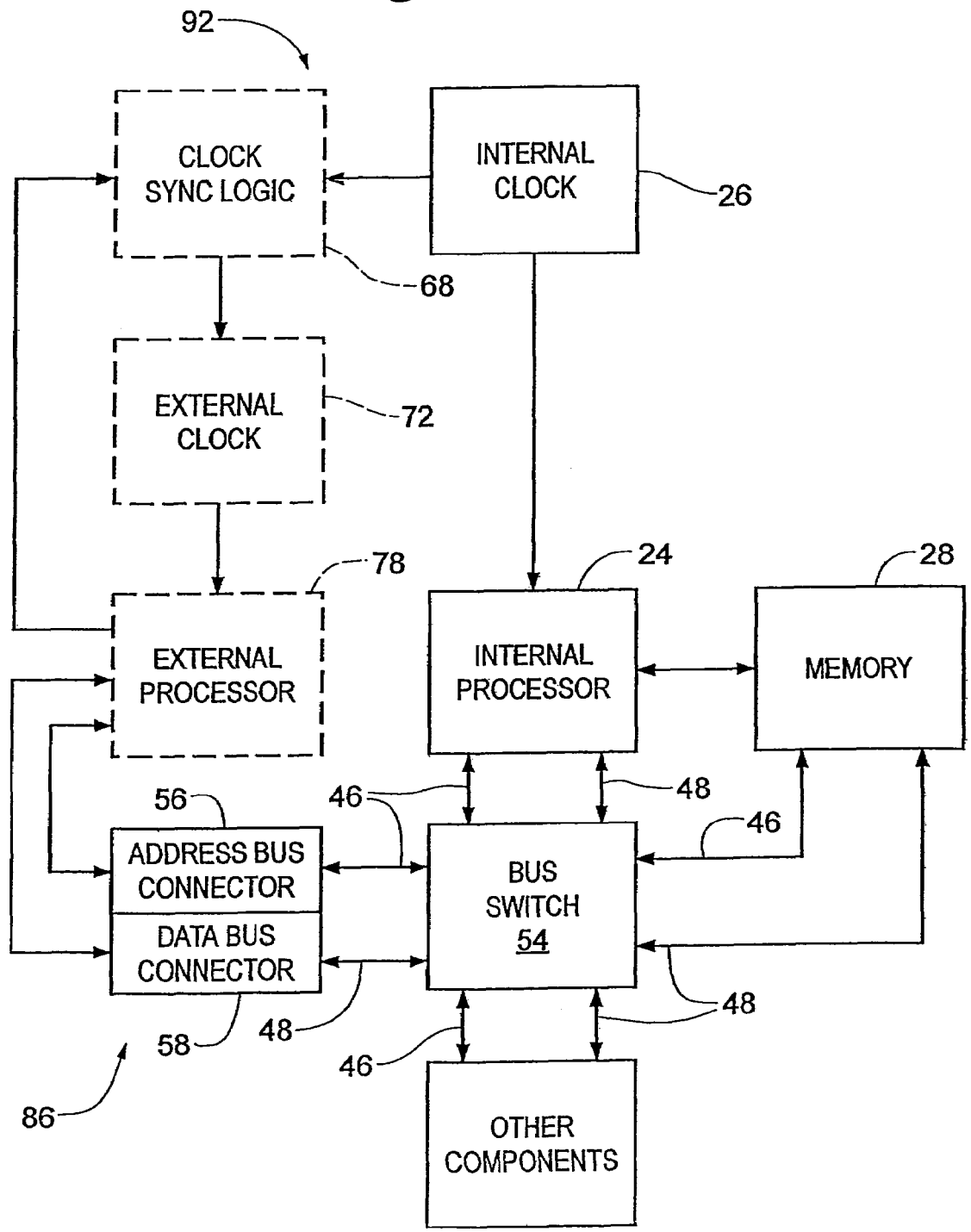
FIG. 5 shows a medical device diagnostic emulation block diagram embodiment.
Figure 6:
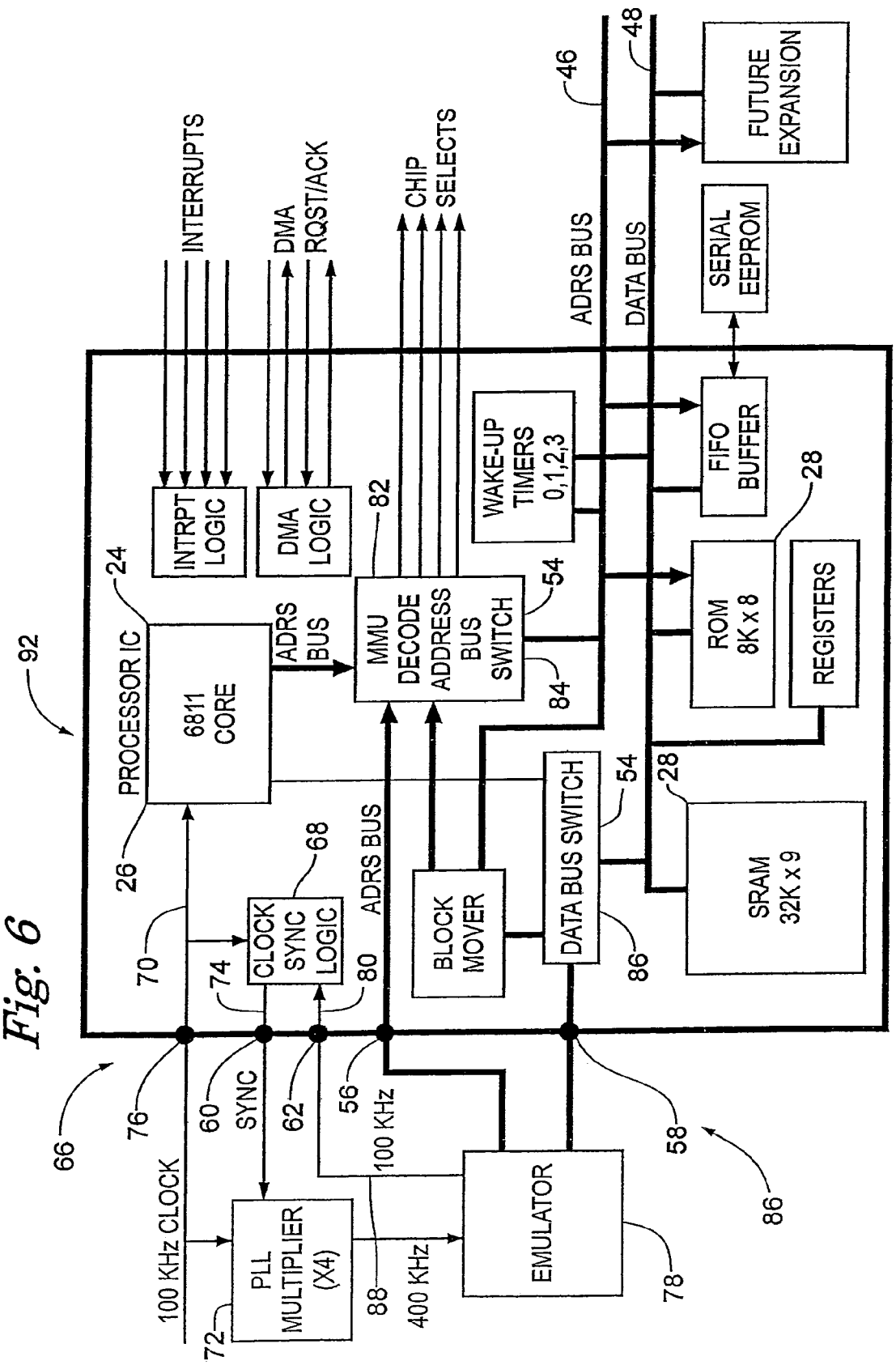
FIG. 6 shows a medical device detailed diagnostic emulation block diagram embodiment.

FIGS. 5 and 6 show block diagrams of an implantable medical device 10 configured for diagnostic emulation embodiment. The implantable medical device 10 configured for diagnostic emulation comprises an internal processor 24, an internal clock 26, memory 28, an address bus 46, a data bus 48, and a bus switch 54. The implantable medical device 10 can also include other components such as found in pacemakers, defibrillators, drug delivery pumps, diagnostic recorders, cochlear implants, the neuro stimulator embodiment described above, and the like. The components are carried in a housing 50 that is hermetically sealed and manufactured from a biocompatible material such as titanium, epoxy, ceramic, and the like. Feedthroughs 52 provide electrical connectivity through the housing 50 while maintaining a hermetic seal. If diagnostic emulation is desired while the medical device 10 is hermetically sealed, separate feedthroughs 52 can be provided or multipurpose feedthroughs 52 can be switched to allow a serialized data stream to recreate an address bus external connection 56, a data bus external connection 58, a clock sync connector 60, and a clock input connector 62. The implantable medical device 10 configured for diagnostic emulation can be a production medical device 10, so the diagnostic emulation results correspond more closely with actual production medical devices 10 than with partially disassembled products or laboratory simulations of products. The internal processor 24 has connectivity to many components of the implantable medical device 10 configured for emulation.

The internal processor 24 can be a micro processor (µP), ASIC state machine, or logic gate array. More specifically the processor 24 can be synchronous and operate on low power such as a Motorola 68HC11 synthesized core operating with a compatible instruction set. The internal clock 26 can operate at a frequency selected for the particular medical device 10 operation such as 100 KHz and greater speeds. The internal clock 26, also known as an oscillator, operates at a frequency compatible with the processor 24, associated components, and energy constraints such as 100 KHz or faster. The calendar clock 64 counts the number of seconds since a fixed date for date/time stamping of events and for therapy control such as circadian rhythm linked therapies. A clock sync circuit 66 includes clock sync logic 68 connected to the internal clock 26 with a clock line 70. The clock sync logic 68 is coupleable to the external clock 72 with a clock sync line 74 that has a clock sync connector 60. The clock line 70 has a clock connector 76 for connecting to the external clock 72. The clock sync logic 68 is coupleable to the external processor 78 with a clock input line 80 that has a clock input connector 62. The clock sync logic 68 synchronizes implantable medical device 10 internal logic with an external clock 72 typically operating at a different speed than the internal clock 26. For example the internal clock 26 can be synchronized with the external clock 72 by causing a rising edge of the internal clock 26 to occur at the same time as a rising edge of the external clock 72. The internal processor 24 is coupled to memory 28.

The memory 28 includes memory sufficient for medical device 10 operation such as volatile Random Access Memory (RAM) for example Static RAM, nonvolatile Read Only Memory (ROM), Electrically Erasable Programmable Read Only Memory (EEPROM) for example Flash EEPROM, and register arrays configured typically on ASICs. Direct Memory Access (DMA) is available to selected modules such as the telemetry module 32, so the telemetry module 32 can request control of the data bus 48 and write data directly to memory 28 bypassing the processor 24. The Memory Management Unit (MMU) 82 allows a larger amount of memory 28 to be addressed such a 1.0 Mb for future programming. Memory 28 is accessed through the address bus 46 and data bus 48.

The address bus 46 is coupled to the internal processor 24, memory 28, bus switch 54, and an address bus external connector 56. The address bus 46 and the data bus 48 are shows as separate lines, but a single line can be used for both the address bus 46 and the data bus 48 if the single line is multiplexed. The address bus 46 and the data bus 48 are bi-directional, which permits the external processor 72 to access internal memory 28. All medical device modules 90 are typically connected to both the address bus 46 and the data bus 48. The address bus 46 operates with a word length compatible with the internal processor 24 such as twenty bit words. The data bus 48 is also coupled to the internal processor 24, memory 28, bus switch 54, and a data bus external connection 58. The data bus 48 operates with a word length compatible with the internal processor 24 such as eight bit words. An example of a bus timing embodiment is shown in Motorola's MC68HC11F1/D Technical Data Rev 3, pp. A-11 and A-12. The address bus 46 and data bus 48 are switched between the internal processor 24 and the external processor 78 with the bus switch 54, so one processor is active and the other processor is inactive.

The bus switch 54 is coupled to the address bus 46, the data bus 48, and the internal processor 24. The bus switch 54 serves as a means for bus switching to selectively switch the address bus 46 and data bus 48 from operation by the, internal processor 24 to configuration for operation by an external processor 78 through the external address bus connection 56 and the external data bus connection 58. The bus switch 54 includes an address bus switch 84 and a data bus switch 86. The address bus switch 84 can be configured in the Memory Management Unit (MMU) 82. The data bus switch 86 can be configured as a group of tri-state logic gates that normally provide control of the data bus 48 to the internal processor 24 and when activated transfer control of the data bus 48 to the external processor 78. The bus switch 54 when activated decouples the internal processor 24 from the address bus 46 and the data bus 48 and couples an external processor 78 to the address bus 46 and data bus 48. The bus switch 54 has connectors 86 for coupling to the external processor 78.

The bus switch 54 has a bus switch external connector 86 that when activated is configured to couple an external processor 78 to the address bus 46 and the data bus 48 and decouple the internal processor 24 from the address bus 46 and data bus 48. The bus switch 54 includes an address bus switch 84 coupled to the address bus external connector 56 and the internal processor 24 and a data bus switch 86 coupled to the data bus external connector 58 and the internal processor 24. The external processor 78 is coupled through the address bus external connection 56 to the address bus 46 and the data bus external connector 58 to the data bus 48. Normally the bus switch 54 couples the internal processor 24 to the address bus 46 and the data bus 48, and the internal processor 24 has control over both the address bus 46 and the data bus 48. When activated by a logic signal the bus switch 54 decouples the internal processor 24, now the inactive processor, from the address bus 46 and the data bus 48. The internal processor 24 is decoupled by the address bus switch 84 switching an internal processor 24 address output to substantially zero, and the data bus switch 86 switching an internal processor 24 data bus output to high impedance. Additionally the bus switch 54 when activated holds the internal processor 24 in a reset condition. When the bus switch 54 is activated the external processor 78, now the active processor, assumes control over the address bus 46 and the data bus 48. The active processor operates and has access to other modules 90 on the address bus 46 and data bus 48. The address bus external connector 56 and the data bus external connector 58 are coupleable to the external processor 78.

The external processor 78, also known as an emulator, can be a micro processor (µP) such as a Motorola 68HC11 operating at a higher speed than the internal processor, an ASIC state machine, a logic gate array, a personal computer or a more powerful computer. The external processor 78 has the capability to execute software and operate the address bus 46 and data bus 48 in a manner compatible with the internal processor 24. The external processor 78 includes memory for executing software and memory for recording software execution history. The software executed by the external processor 78 can be testing software to record operation of the implantable medical device 10 during testing and operating software to operate the implantable medical device 10 according to a test program. The testing software will typically have the capability to set a break point to stop execution of the operating software at a certain address. The testing software can reach results such as detection of nonconformance in medical device 10 hardware, firmware, and software. The external processor 78 can have an external clock 72 to enable the external processor 78 to operate at higher speeds than the internal processor 24 to reduce diagnostic testing time.

The external clock 72 can be a separate clock that is synchronized with the internal clock 26 or a Phase Lock Loop (PLL) multiplier connected between the clock connection 76 and the external processor 78. For example if the internal clock 26 is operating at 100 KHz and the PLL is a four times multiplier, then the external processor 78 will have a clock speed of 400 KHz. A clock divider will typically be placed between the external processor 78 and the clock sync logic 68 to provide an external processor clock input 88 to the clock sync logic 68. The clock divider can be integral to the external processor 78. The clock divider converts the external clock 72 to the frequency of the internal clock 26 for an input to the clock sync logic 68 to drive implantable medical device 10 components other than the internal processor 24 at the speed the components are designed to operate. Examples of clock connection embodiments are shown in Motorola's MC68HC11F1/D Technical Data Rev 3, pp. 2-4 and 2-5. Implantable medical devices typically use functional modules to perform functions.

A functional module 90 is connected to the address bus 46 and the data bus 48. The functional module 90 is a module from an implantable medical device 10 such as found in neuro stimulators, pacemakers, defibrillators, drug delivery pumps, diagnostic recorders, cochlear implants, and the like. For an implantable neuro stimulator 12 embodiment, the functional module 90 can be a therapy module 40, therapy measurement module 42, power management module 38, recharge module 34, telemetry module 32, and the like. Operationally coupling an implantable medical device 10 configured for emulation to an external processor 78 forms an emulation system.

An emulation system 92 comprises an internal processor 24, an internal clock 26, memory 28, an address bus 46, a data bus 48, an external processor 78, an external clock 72, and a bus switch 54. The internal clock 26 and memory 28 are both coupled to the internal processor 24. The address bus 46 is coupled to the internal processor 24 and memory 28. The data bus 48 is also coupled to the internal processor 24 and memory 28. The external processor 78 is coupled to the address bus 46 and the data bus 48. The external clock 72 is coupled to the external processor 78. A clock sync circuit 66 is connected between the external clock 72 and the internal clock 26 to synchronize internal logic with the external clock 72. A bus switch 54 is coupled to the address bus 46, the data bus 48, and a bus switch connector 86. The bus switch 54 when activated decouples the internal processor 24 from the address bus 46 and the data bus 48 and couples the external processor 78 to the address bus 46 and the data bus 48. The emulation system 92 can operate according to the following method.

Figure 7:
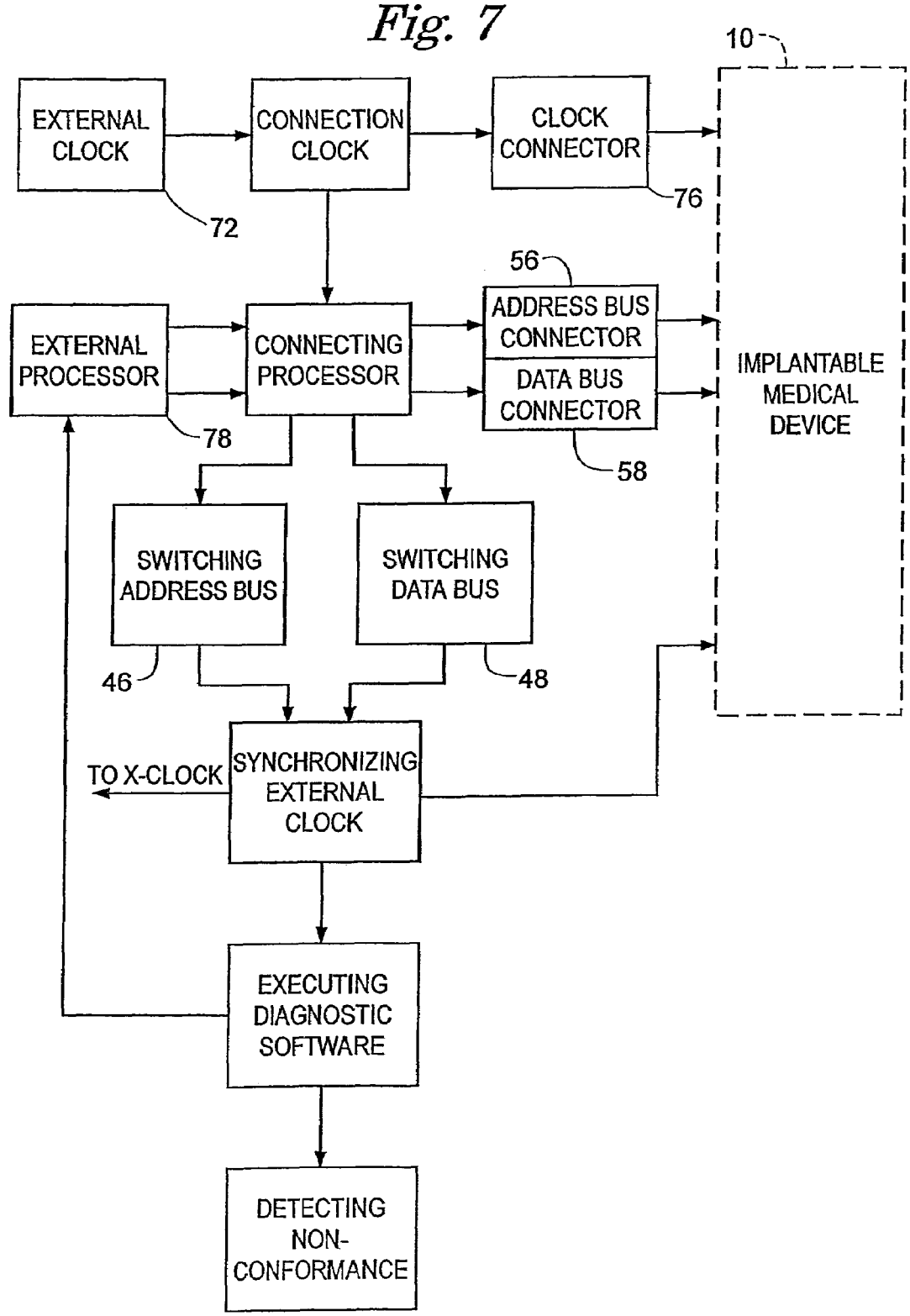
FIG. 7 shows a medical device method of diagnostic emulation embodiment.

FIG. 7 shows a method for implantable medical device 10 diagnostic emulation embodiment, and FIG. 6 shows a block diagram of an implantable medical device 10 configured for emulation embodiment. The method includes the following steps that are not necessarily listed in order. An external clock 72 is connected to a clock external connector 76. An external processor 78 is connected to an address bus external connection 56 and a data bus external connection 58. The address bus 46 is switched from the internal processor 24 to the external processor 78. Switching the address bus 46 can be accomplished by holding the inactive processor address at zero. The Memory Management Unit (MMU) 82 can serve as the address bus switch 84 by forcing the inactive processor address bus 46 to zero. Since the MMU 82 uses the sum of the two addresses from the external processor 78 and internal processor 24 to perform its calculations, the inactive processor is excluded from addresses. The data bus switch 86 switches the data bus 48 from the active processor to the inactive processor. Although the data bus 48 for the internal processor 24 and external processor 78 are connected together, the data bus switch 86 holds the inactive processor data bus connection in a high impedance state so that the inactive processor does not affect the active processor data bus 48. Some embodiments can also include additional elements such as medical device processor software executed with the external processor 78. The external processor 78 can also execute additional software to detect nonconformance in the medical device 10. Additional embodiments are also possible. Synchronization of the internal clock 26 and the external clock 72 can be better understood by examining their timing.

Figure 8:
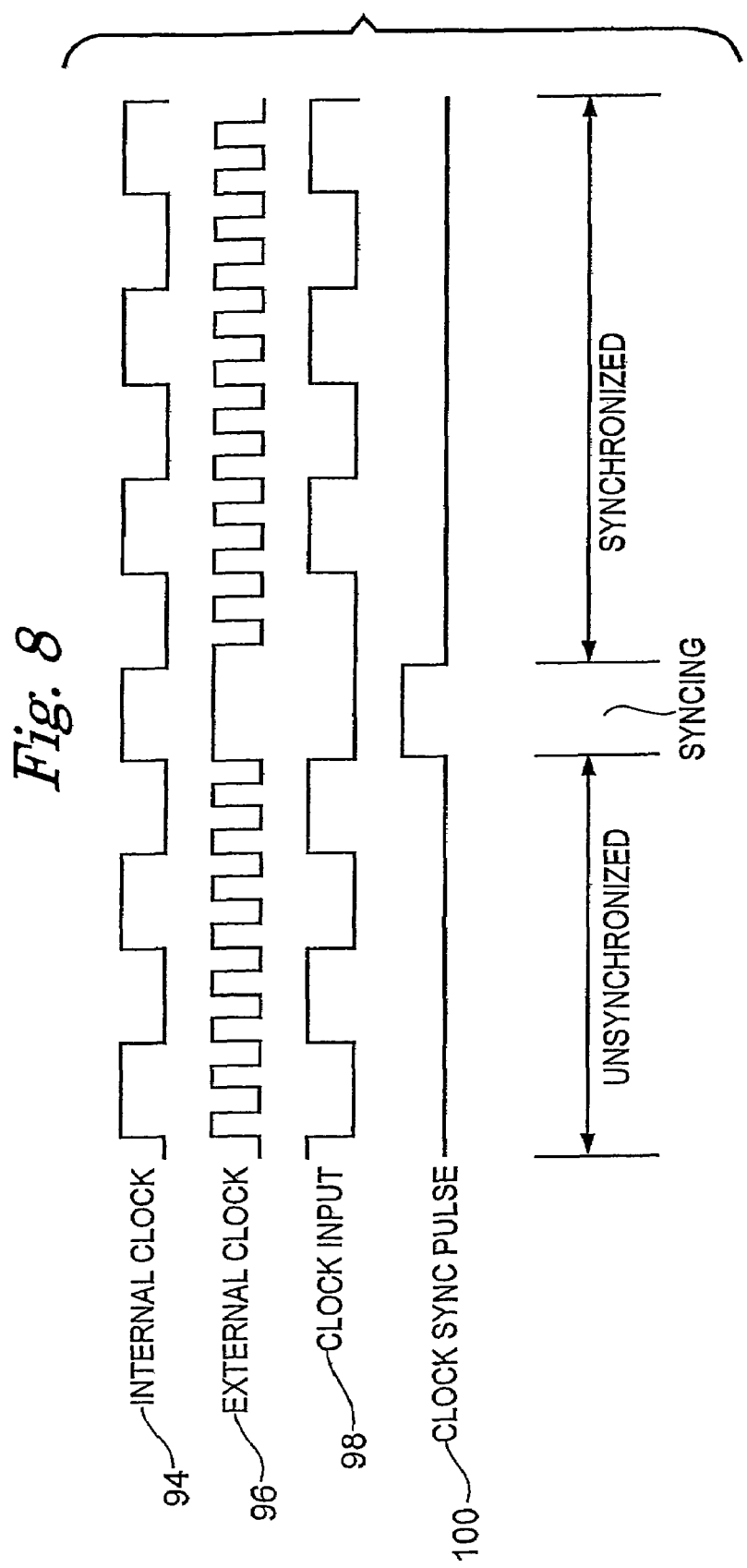
FIG. 8 shows a clock synchronization timing diagram embodiment.

FIG. 8 shows a clock synchronization timing diagram embodiment with the internal clock pulse 94, external clock pulse 96, and external processor clock pulse 98. In some embodiments, the method can also include synchronizing the external clock 72 to the internal medical device logic. Synchronization occurs by lining up the leading edge of the internal clock pulse 94 with the external clock pulse 96 and the external processor clock pulse 98. The synchronization pulse 100 is generated by the clock sync logic 68.

Figure 9:
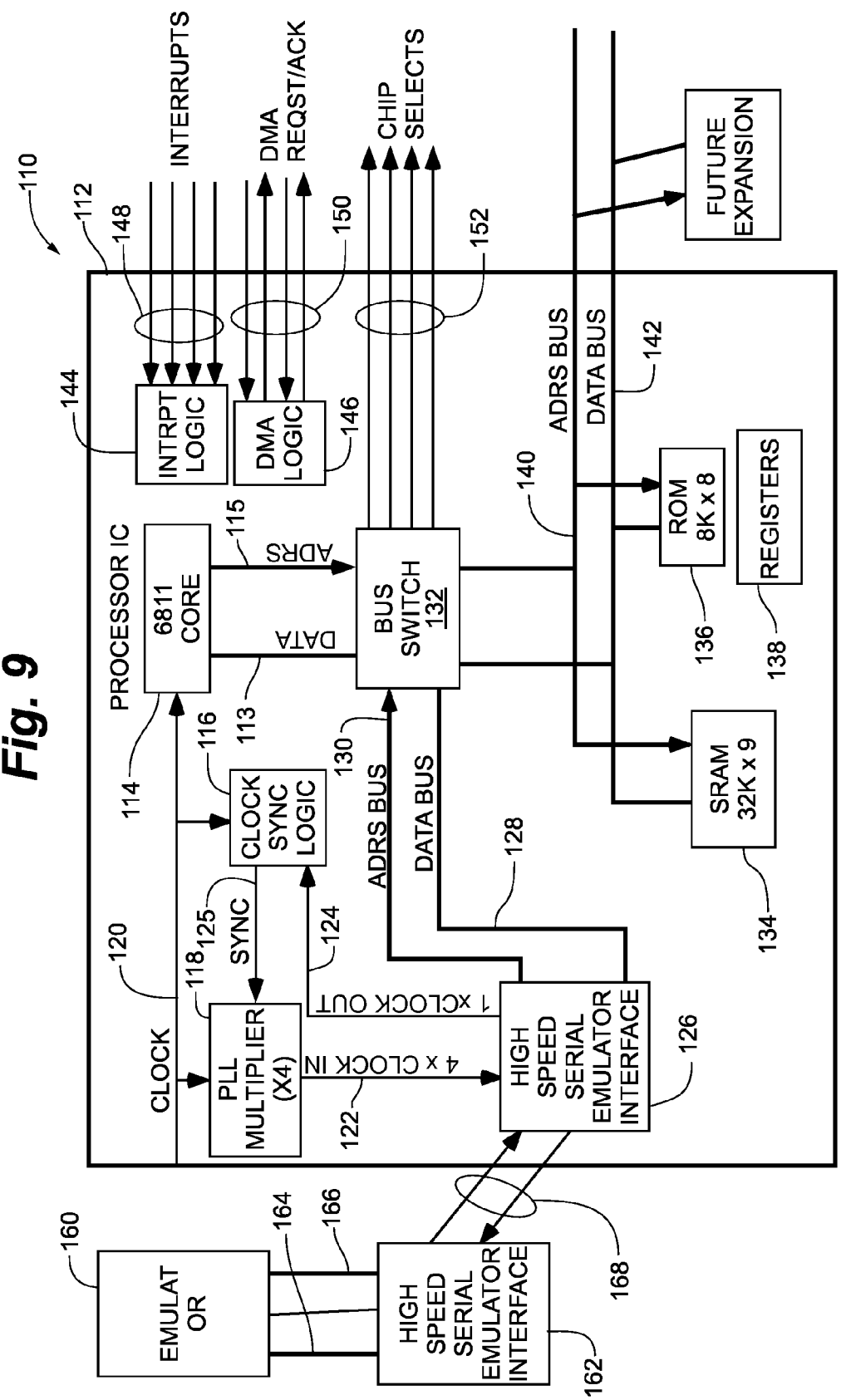
FIG. 9 shows a block diagram of an implantable medical device having an a high speed serial emulator interface coupled to an external emulator having a high speed emulator interface.

FIG. 9 illustrates a diagnostic emulation system 110 for device external operation. Diagnostic system 110 includes generally an emulator 160 and an implantable medical device (IMD) 112. IMD 112 may be viewed as a circuit board or other substrate having electronic components thereon and may also, in other contexts, be viewed as a circuit board or other substrate disposed within a hermetically sealable or hermetically sealed case, depending on the embodiment. IMD 112, as illustrated in FIG. 9, does not necessarily show all levels of detail or all components not directly related to the present invention.

Emulator 160, in the embodiment shown, is coupled to a high speed serial emulator interface 162 through a parallel address bus or address line 166 and through a parallel data bus or data line 164. High speed serial emulator interface 162 is coupled to an internal high speed serial emulator interface 126 through a bi-directional serial channel 168. External high speed serial emulator interface 162 can receive parallel address and data information through buses 164 and 166, and convert this information into serial format for communication through serial channel 168. The serial format data received by high speed serial emulator interface 126 can then be changed back to parallel format and put onto an internal address bus 130 and an internal data bus 128. The address bus 130 and data bus 128 can then be coupled through buses switch 132 to read and write SRAM or memory location 134 and registers 138 and to read ROM memory location 136 through address bus 140 and data bus 142. In normal IMD operation, bus switch 132 is set to allow processor 114 to control address bus 140 and data bus 142 through address bus 115 and 113 disposed between processor 114 and bus switch 132. When bus switch 132 receives an activation signal, the bus switch can switch to allow control of address bus 140 through address bus 130 and data bus 142 through data bus 128. Such activation signal can be transmitted through a physical connection, but is more often transmitted through use of a magnetic reed switch or other magnetically sensitive switch, or through reception of a telemetry signal.

The external emulator 160 can thus control external address bus 166 and external data bus 164 that are then coupled to control address bus 130 and data bus 128 and to then control address bus 140 and data bus 142. This control is accomplished by converting the parallel emulator outputs through high speed serial emulator interface 162 and then reconverting the serial signal through high speed serial emulator interface 128 back to parallel signals. Emulator 160 can thus replace processor 114 to control the address bus and data bus within IMD 112. This control is preferably performed at the same speed as that of normal operation of IMD 112. Specifically, in some methods, address bus 140 and data bus 142 are both operated at the same speed, whether under control of internal processor 114 or external emulator 160. In other embodiments, address bus 140 and data bus 142 may be operated at speeds slower than or greater than the normal operating speed as seen by the buses.

IMD 112 may now be explained further. A clock line 120 may be seen coupled to a phase lock loop (PLL) multiplier 118 to multiply the clock signal 120×4 and output the 4× clock signal through another clock line 112 to high speed serial emulator interface 126. A 1× clock output signal 124 may be seen coupled to clock sync logic 116, which is also coupled to clock line 120. Clock line 120 can be used to provide a clock signal to processor 114 and to allow synchronization of external emulator 160 with internal processor 114, as previously discussed.

IMD 112 also includes interrupt logic 144 for receiving interrupt lines 148. DMA logic 146 may also be seen, including lines 150 for reading and writing DMA data. Chip select lines 152 may also be seen, coupled to bus switch 132. Chip selects 152 may be used to address multi-function chips, for example, those chips used to interact with the telemetry devices, with the battery charging signals, and with the signals output to the body or input from the body from the physiological modules and leads attached to IMD 112.

Figure 10:
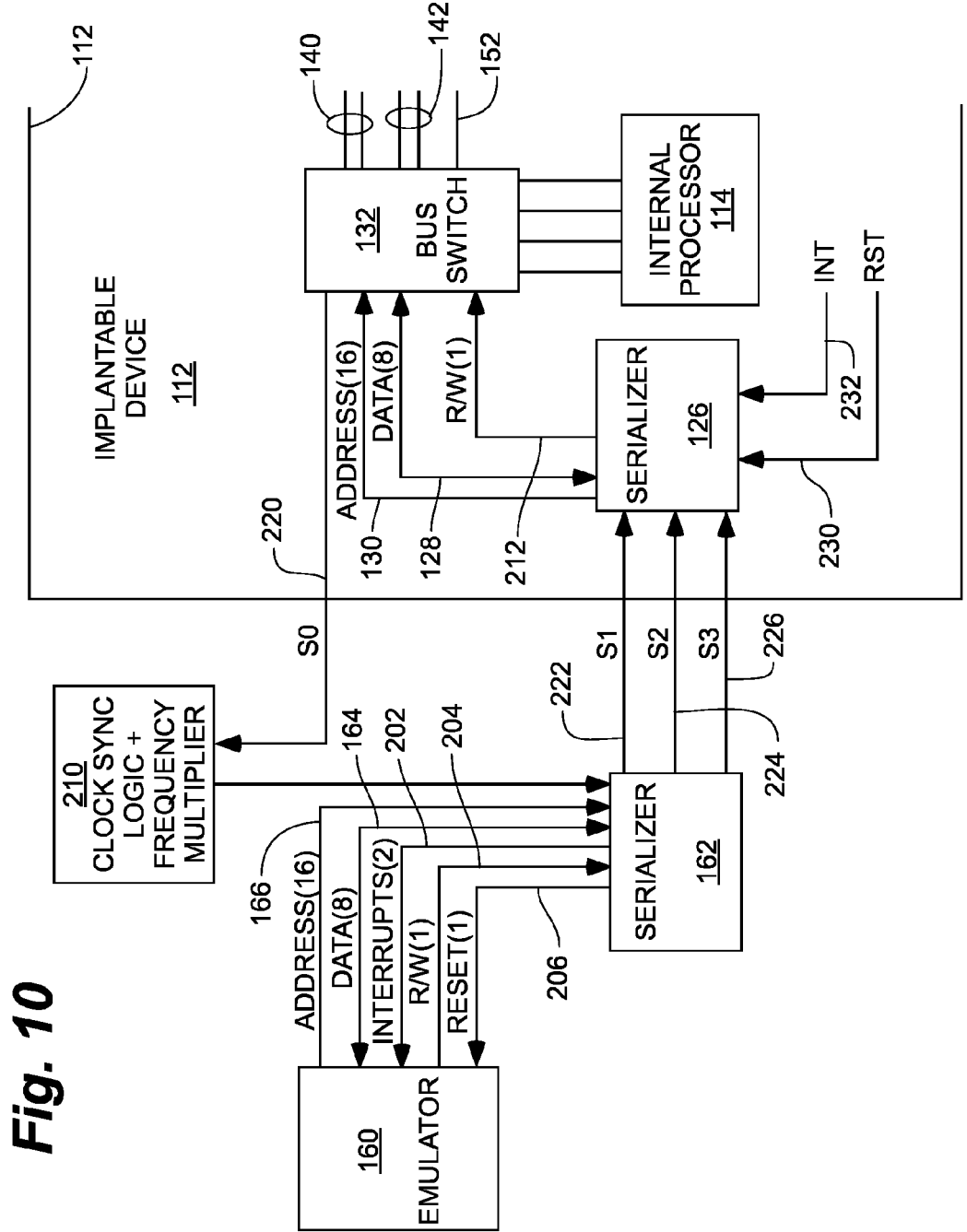
FIG. 10 shows a block diagram of an implantable medical device system having a serial emulator port.

FIG. 10 illustrates IMD 112 in greater detail. Emulator 160 is coupled to serializer 162, which is also referred to as a external high speed serial emulator interface 162. In addition to external address bus 166 and data bus 164, interrupt lines 202 and reject line 206 may be seen being communicated from serializer 162 to emulator 160. This can be used to update the state of external emulator 160 to match the state that the internal processor would have, given the interrupt and reset information available in normal use. A read/write line 204 may also be seen, for communicating to serializer 162. Read/write line 204 can be used to indicate to serializer 162 that the address on address bus 166 is to either be read from IMD 112 or written to IMD 112, using the data on data bus 164.

Extending between IMD 112 and the external emulator system, a clock sync line 220 labeled "SO" may be seen coupled to clock sync logic and frequency multiplier 210. Clock sync line 220 can be used to output the timing information of the internal clock to the external clock sync logic 210, thereby allowing the external emulator system to be in sync with the internal processor, as previously discussed. Three serial communication lines are illustrated in FIG. 10, including a first serial input line 222, labeled "S1", a second serial input line 224, labeled "S2", and a third, output serial line, labeled "S3" at 226. Parallel data received by internal serializer 126 from serial lines 222 and 224 can be converted to parallel data and put onto address bus 130, data bus 128, and read/write line 212. Similarly, data read from address bus 130, and read/write line 212 can be output through third serial line 226.

Interrupts 232 and reset 230 may be seen coupled to serializer 126. Serializer 126 can receive parallel information from interrupt lines 232 and reset line 230, and add them to the serial data stream being output through serial output line 226.

In use, emulator 160 can set an address on address bus 166, set data on data bus 164 to be written at that address, set the read/write line 204 to write, with the address, data, and read/write signals output in serial format through serial lines 222 and 224 (after being converted into serial format by serializer 162). Serial data from serial lines 222 and 224 can be converted by serializer 126 back into parallel format on address bus 130, data bus 128, and read/write line 212. The data can then be written out through or to address bus 140, data bus 142, and chip select lines 152.

Similarly, when a read of an address is desired by external processor 160, the address can be put onto address bus 166 and read/write line 204 be set to indicate a read. After the address has been put onto address lines 140 by bus switch 132, the data can be returned on data bus 142 and data bus 128, be serialized, and transmitted over serial line 226 to external serializer 162 and then to emulator 160.

As IMD 112 will have its state changed by any reset signals and interrupt signals, such information must be provided to emulator 160 as well. These bits of information are transmitted in serial form across serial line 226, in this embodiment of the invention. Serial lines S1, S2, and S3 may also include a ground line or sheath in order to provide a better signal.

Serializers 162 and 126 may also be referred to as parallel-serial converters, serial-parallel converters, serial-parallel interfaces, and serial-parallel interfaces. Devices to convert between parallel and serial communication are very well known, are common place, and are, for example, used in personal computers to effect serial communication. Such serializer devices often work by writing parallel data into shift registers, then shifting out the contents of the shift register in serial fashion out through the serial line. Similarly, data can be written bit by bit into the shift register, with the data read out in parallel fashion after the shift register is full.

Figure 11:
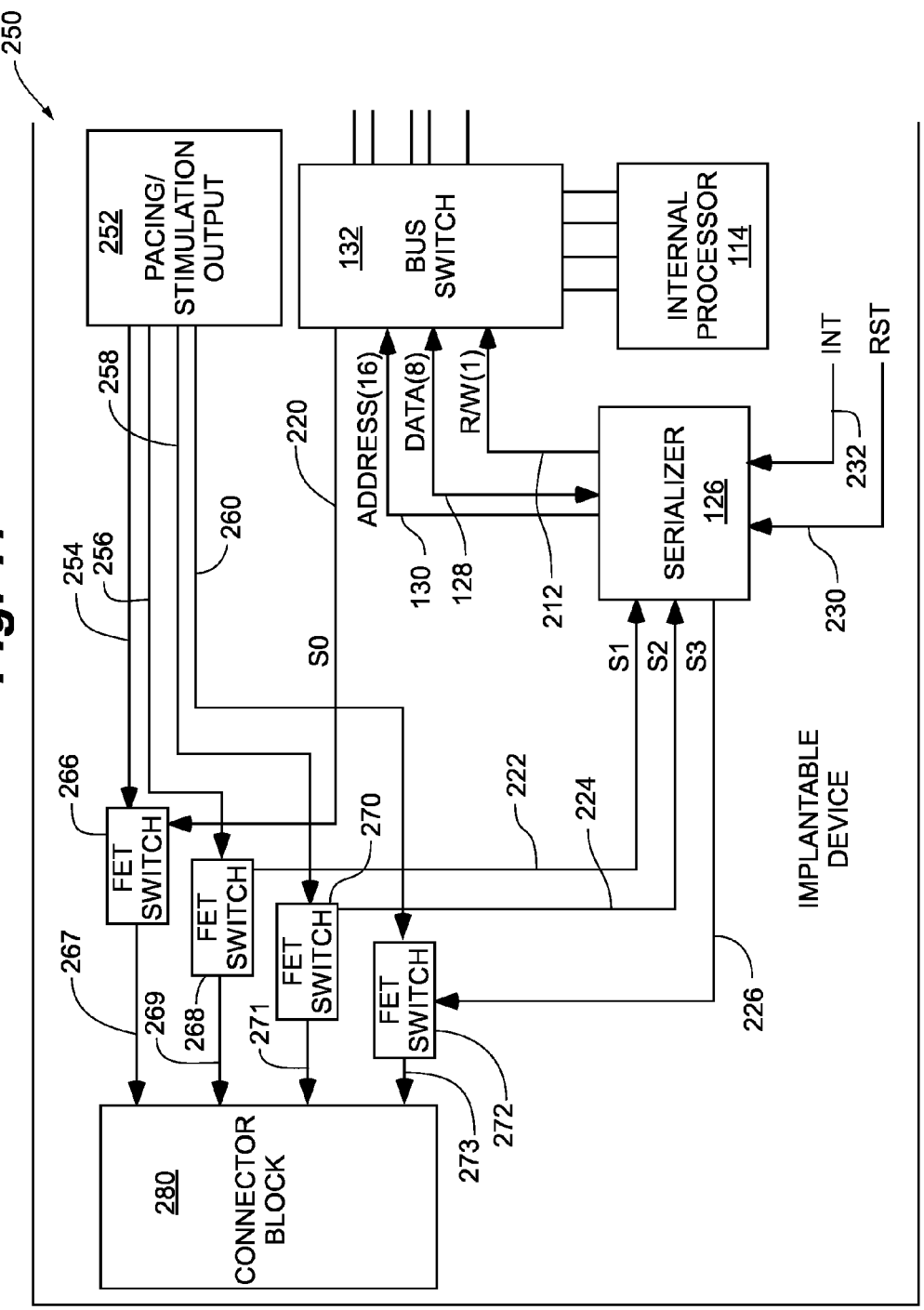
FIG. 11 shows a block diagram of a subsystem for providing external emulator communication through an existing pacing or stimulation lead connector.

FIG. 11 illustrates another external emulation system 250 including some identical elements previously discussed and identically numbered. In system 250, serial lines 220, 222, 224, and 226 are output through an external connector block 280, which is normally used for coupling to a biomedical electrical lead. Connector block 280 can used normally to send cardiac pacing signals, cardiac defibrillation signals, neurological pain relief stimulation signals, or to send or receive any other medially-related electrical signals. A pacing/stimulation output block 252 may be seen coupled to four output lines 254, 256, 258, and 260. These lines, respectively, are coupled to FET switches 266, 268, 270, and 272. These FET switches are coupled, respectively, through a shared output line 267, 269, 271, and 273. The FET switches thus can control whether communication between connector block 280 is with serializer 126 or with pacing/stimulation output block 252.

In use, the normal electrical stimulation lead may be removed from connector block 280, and a compatible electrical connection inserted into connector block 280 to allow communication with serializer 126. Internal processor 114 can thus be decoupled and bus switch 132 set to access, or allow access, from an external serializer through connector block 280 to the controllable and readable components of the implantable medical device. In another method, the electrodes on the lead normally used for electrical stimulation are coupled to an external emulator of the implantable medical device and used to perform emulation. As before, the switching of the FETs can be controlled by a mechanism such as a magnetic switch, a telemetry command, and the like. This can be done while the circuit of the IMD is not yet in the hermetically sealed housing, after it has been in the sealable housing but not yet sealed, and after the housing has been hermetically sealed, and also after the hermetically sealed housing has been implanted in a body.

Figure 12:
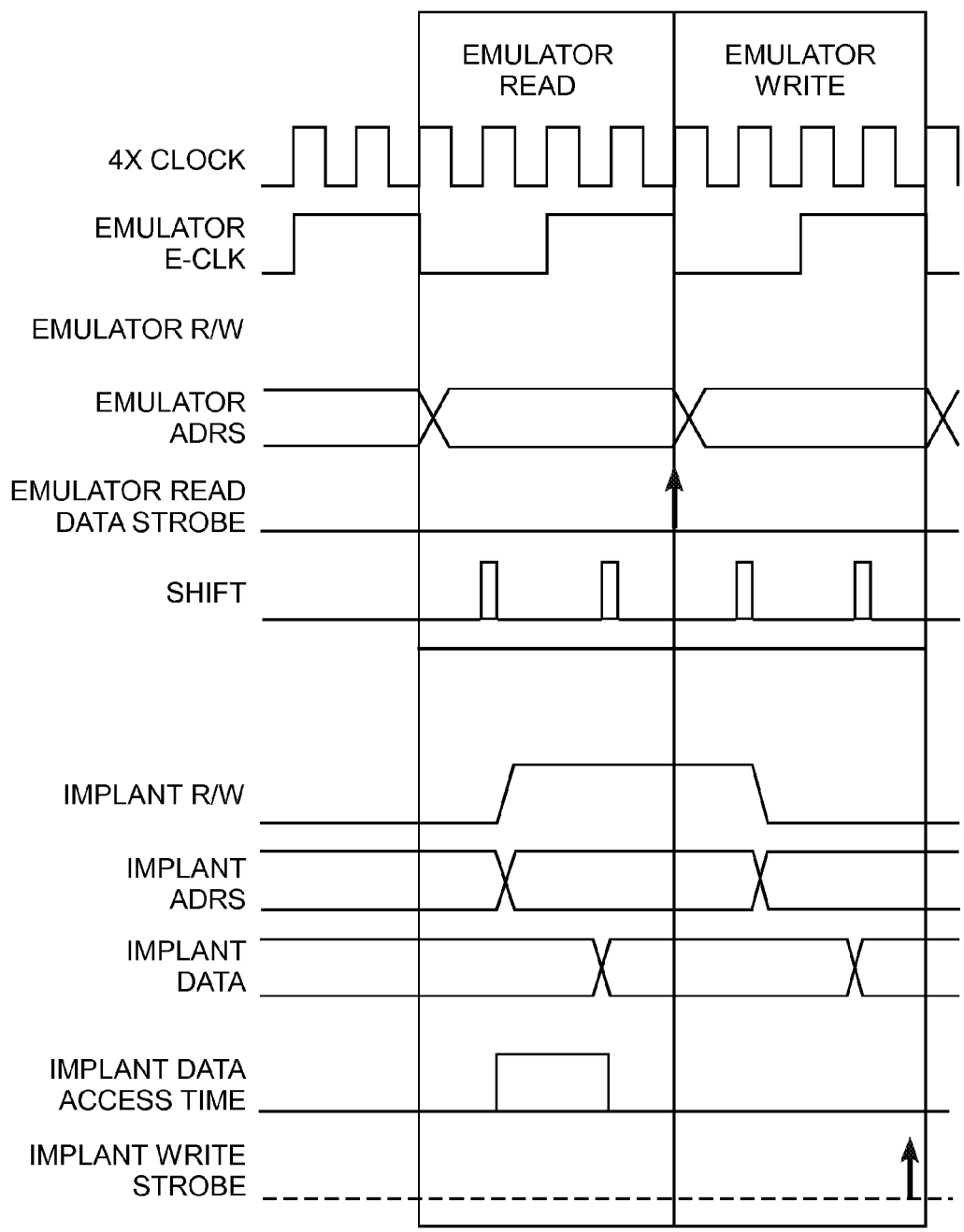
FIG. 12 shows a timing diagram of an emulator read/write cycle.

FIG. 12 illustrates the timing of one embodiment of the invention. As previously discussed, in some embodiments, the date, address, chips select, and other lines and buses within the IMD are accessed at same speed as they would be were the internal processor, rather than the external emulator, in control of the device. During a read cycle in this embodiment, two serial data transfers must occur. The first must occur at the middle of the first half clock cycle after that address and the R/W line is stable. This first transfer sends the status of the address and control lines from the emulator to the device. The second must occur at the middle of the second half clock cycle after the read data has been placed on the bus. It returns the state of the device lines back to the emulator. During a rate cycle, two serial data transfers must occur. The first must occur at the middle of the first half clock cycle after that address and R/W line is stable. The first sends the state of the address and control lines from the emulator to the device. The second must occur at the middle of the second half clock cycle after the right data has been placed on the bus. It sends the state of the emulator data lines to the device. The immediately preceding discussion about the requirements for the read and right cycle timings are applicable to some embodiments of the invention where the timing of the IMD during external emulation is the same as timing during normal internally controlled operations.

The frequency of the shift clock for this embodiment is constrained by the address valid time, the data access time, and the data set up time prior to emulate or read. Two complete shifts of sixteen bits must be completed within this time period, and in this embodiment. This may be given by the equation:

$$Fshclk > 32/(Teper - Trdsetup - Tadvalid - Taccess))$$

Where:
Fshclk=Minimum frequency of the shift clock
Teper=Period of E-Clock (Bus Cycle)
Trdsetup=Setup time for external (emulator) read
Tadvalid=Delay from E-clock falling edge to Address Valid
Taccess=Worst case access of internal data (memory, registers)

The amount of information being sent to the device and the amount being returned is not symmetrical: 16 address+8 data+1 R/W line is sent to the device and 8 data bits plus 2 interrupt plus 1 reset are returned from the device. The clock sync line cannot be serialized and is sent directly in some embodiments. To minimize serial data latency, it is desirable to balance the sent and received data strings. This is accomplished by dividing the sent data into two serial strings each 16 bits in length. The serial data is a serial string of 16 bits length. Pad bits may be added where necessary to allow symmetrical string lengths and to allow for any future expansion that may be desirable.

Figure 13:
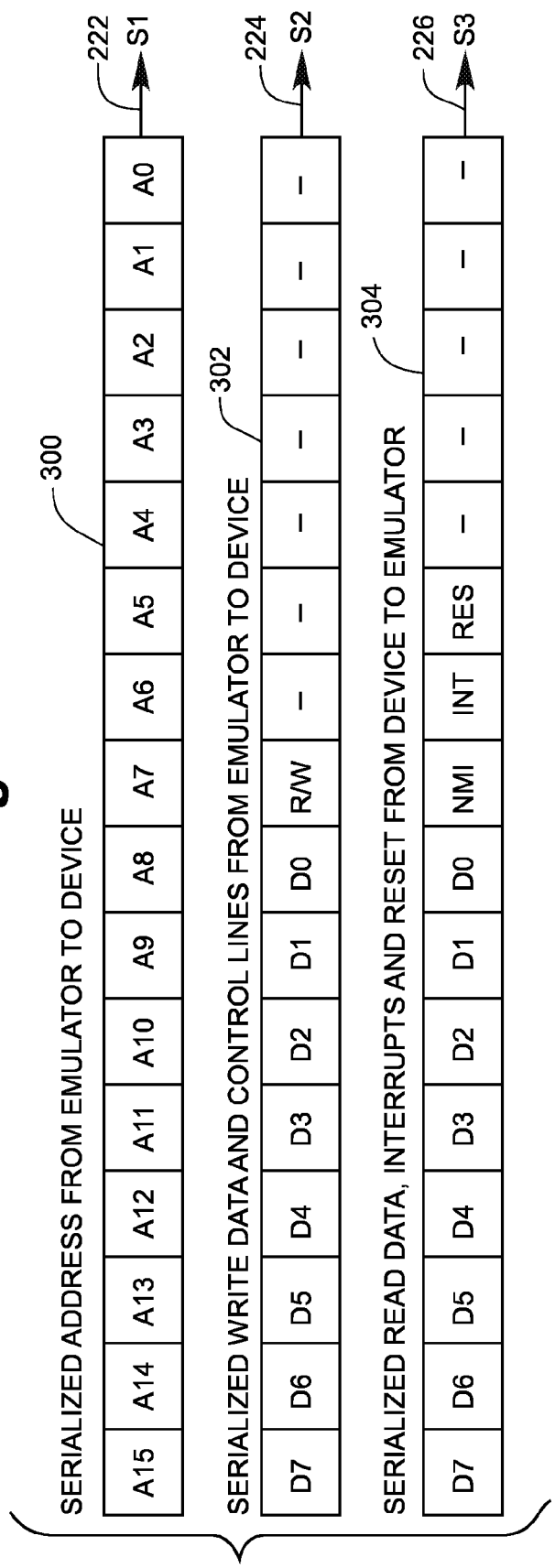
FIG. 13 shows an example of serialized address and data.

FIG. 13 shows a first register 300 to be sent through serial line 222, a second register 302 to be sent through serial line 224, and a third register 302 that has been read from serial line 226. Register 300 includes sixteen address bits in the embodiment illustrated. Second register 302 includes eight data bits and one R/W bit indicating whether the address in register 300 is to be read to or written from. Third register 304 includes eight more data bits, and NMI bit, (nonmascial interrupt), an interrupt bit, and a reset bit.

Thus, embodiments of an implantable medical device configured for diagnostic emulation are disclosed that enhance diagnostic testing with capabilities such as faster testing, and more realistic testing. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A medical device (MD) configured for diagnostic emulation including being configured for coupling to an external processor, the MD comprising:
   an internal processor;
   an internal clock coupled to the internal processor;
   memory;
   a bus switch coupled to the internal processor and to the memory to read and write to the memory;
   a first address bus coupling the internal processor to the bus switch;
   a first data bus coupling the internal processor to the bus switch;
   a second address bus coupled to the bus switch;
   a second data bus coupled to the bus switch;
   wherein the bus switch is adapted to receive an activation signal, wherein upon receiving the activation signal the bus switch is configured to couple the second address bus to the memory, couple the second data bus to the memory, and decouple the internal processor from the memory; and
   a serial-parallel interface having a serial communications port, and a parallel port coupled to the second address bus and the second data bus, wherein the serial-parallel interface is configured to receive a serial format address through the serial communications port and output a parallel format address to the second address bus through the parallel port.

2. The MD of claim 1, further comprising at least one interrupt line coupled to the serial-parallel interface, in which the serial-parallel interface is configured to output data from the interrupt line in serial format through the serial communication port.

3. The MD of claim 1, in which the serial port includes at least one output line and one input line.

4. The MD of claim 1, in which the serial port includes at least one output line and two input lines.

5. The MD of claim 1, farther comprising a plurality of electrically conductive lines and a feedthrough connector, the electrically conductive lines being coupled to the serial-parallel interface serial communication port and to the feedthrough connector.

6. The MD of claim 1, further comprising:
an electrical stimulator having stimulator output lines;
a feedthrough connector including a plurality of connections for electrically coupling to an external electrical device;
a switch coupled to the stimulator output lines and to the serial-parallel interface serial communication port and to the feedthrough connector, wherein the switch is configured to establish electrical continuity between the feedthrough connector and either the serial-parallel interface serial communication port or the stimulator output lines, but not both at the same time, such that the serial-parallel interface serial communication port can be communicated with through the feedthrough connector.

7. The MD of claim 1 wherein the MD is substantially a production MD.

8. The MD of claim 1 wherein the bus switch when activated decouples the internal processor from the first address bus and the first data bus by switching an internal processor address output to substantially zero and switching an internal processor data bus output to high impedance.

9. The MD of claim 1 wherein the internal processor has a reset condition, wherein the bus switch when activated holds the internal processor in the reset condition.

10. The MD of claim 1 wherein the bus switch comprises an address bus switch and a data bus switch, wherein the address bus switch is coupled to the first and second address buses and the data bus switch is coupled to the first and second data bus.

11. The MD of claim 10, further comprising a memory management unit wherein the address bus switch is part of the memory management unit.

12. The MD of claim 10 wherein the data bus switch comprises tri-state logic gates.

13. The MD of claim 1, wherein the MD is adapted to be coupled to an external clock, the MD further comprising:
clock sync logic;
an external clock connector for coupling to the external clock; and
a clock line coupling the clock sync logic to the internal clock and the external clock connector.

14. The MD of claim 13 wherein the MD includes internal logic, wherein the external and internal clocks operate at different speeds, and wherein the clock sync logic synchronizes the MD internal logic with the external clock.

15. The MD of claim 1, further comprising a functional module coupled to the bus switch.

16. The MD of claim 15 wherein the functional module performs a function selected from the group of functions consisting of: therapy, therapy measurement, power management, recharge, and telemetry.

17. The MD of claim 1 wherein the MD is selected from the group consisting of: a neuro stimulator, a pacemaker, a defibrillator, a drug delivery pump, a diagnostic recorder, and a cochlear implant.

18. The MD of claim 1, in which the MD is configured to be hermetically sealed and implanted in a human body.

19. The MD of claim 18, in which the MD includes a hermetically sealable housing.

20. The MD of claim 18, in which the MD is hermetically sealed within a housing.

21. The MD of claim 1, in which the internal processor is selected from the group consisting of microprocessors, ASIC state machines, and logic gate arrays.

22. A medical device (MD) configured for diagnostic emulation including being configured for coupling to an external processor, the MD comprising:
an internal processor;
an internal clock coupled to the internal processor;
memory coupled to the internal processor in a parallel format connection;
a first address bus coupling the internal processor to the memory;
a first data bus coupling the internal processor to the memory;
a second address bus;
a second data bus;
means for receiving an externally generated activation signal;
means for bus switching to selectively switch the memory from operation by the internal processor through the first address and first data bus to configuration for operation by the external processor through the second address bus and second data bus, responsive to reception of the externally generated activation signal;
means for sending and receiving serial data communication to and from the MD;
means for converting serial format data into parallel format coupled to the second address bus and second data bus; and
means for converting the parallel format data to serial format coupled to the second address bus and second data bus.

23. The MD of claim 22, wherein the MD includes interrupt data, wherein the means for converting parallel format data to serial format data is configured to convert the interrupt data into serial format.

24. The MD of claim 22, further comprising:
means for housing contents of the MD;
means for electrically stimulating a patient;
means for connecting to an external electrical signal;
means for switching the electrically stimulating means and a serial-parallel interface means through to the external connecting means, wherein the switching means is configured to put the external connecting means in electrical communication with either the stimulating means or the serial-parallel interface means but not both at the same time, such that the means for serial-parallel interface can be communicated with from outside of the housing.

25. The MD of claim 22, wherein the MD includes internal logic, wherein the internal clock and an external clock operate at different speeds, further comprising means for clock synchronization to synchronize the MD internal logic with the external clock.

26. The MD of claim 22, in which the internal processor is selected from the group consisting of microprocessors, ASIC state machines, and logic gate arrays.

27. The MD of claim 22 further comprising a hermetically sealed housing and a feedthrough providing electrical connectivity extending through a housing external connecting means.

* * * * *

UNITED STATES PATENT AND TRADEMARK OFFICE
CERTIFICATE OF CORRECTION

PATENT NO.       : 7,289,852 B2                                    Page 1 of 1
APPLICATION NO.  : 10/955596
DATED            : October 30, 2007
INVENTOR(S)      : Helfinstine et al.

It is certified that error appears in the above-identified patent and that said Letters Patent is hereby corrected as shown below:

Col. 13, Line 14: "farther" should read --further--

Signed and Sealed this

Twenty-fifth Day of November, 2008

JON W. DUDAS
*Director of the United States Patent and Trademark Office*